(12) United States Patent
Chikatsune et al.

(10) Patent No.: US 7,482,485 B2
(45) Date of Patent: Jan. 27, 2009

(54) METHOD FOR EXTRACTING SLURRY

(75) Inventors: Tetsuya Chikatsune, Ehime (JP); Hiroshi Horiuchi, Ehime (JP)

(73) Assignee: Teijin Limited, Osaka (JP)

( * ) Notice: Subject to any disclaimer, the term of this patent is extended or adjusted under 35 U.S.C. 154(b) by 0 days.

(21) Appl. No.: 10/591,249

(22) PCT Filed: Mar. 3, 2005

(86) PCT No.: PCT/JP2005/004141

§ 371 (c)(1),
(2), (4) Date: Aug. 31, 2006

(87) PCT Pub. No.: WO2005/084789

PCT Pub. Date: Sep. 15, 2005

(65) Prior Publication Data

US 2007/0179313 A1  Aug. 2, 2007

(30) Foreign Application Priority Data

Mar. 5, 2004 (JP) ............................. 2004-062331

(51) Int. Cl.
*C07C 63/32* (2006.01)
*B04B 1/20* (2006.01)

(52) U.S. Cl. ........................................ 562/485; 494/37

(58) Field of Classification Search ................ None
See application file for complete search history.

(56) References Cited

U.S. PATENT DOCUMENTS 5,502,247 A * 3/1996 Bartos et al. ................ 562/486
5,919,977 A * 7/1999 Murakami et al. .......... 562/412
2002/0154569 A1  10/2002 Burnett et al.

FOREIGN PATENT DOCUMENTS

| EP | 0 860 423 A1 | 8/1998 |
| JP | 8-89706 A | 4/1996 |
| JP | 8-89706 A1 | 4/1996 |
| JP | 08-141386 A | 6/1996 |
| JP | 10-216661 A | 8/1998 |
| JP | 10-291957 A | 11/1998 |
| JP | 11-128612 A | 5/1999 |
| JP | 2003-128624 A | 5/2003 |

* cited by examiner

*Primary Examiner*—Daniel M Sullivan
*Assistant Examiner*—Louisa Lao
(74) *Attorney, Agent, or Firm*—Sughrue Mion, PLLC

(57) ABSTRACT

A major object of the invention is to provide such a method for extracting slurry that is not inhibited in extraction of slurry by a released and accumulated matter or a solid matter sedimented and accumulated at the bottom of the vessel. The invention relates to a method for extracting slurry by extracting slurry from an agitation vessel having a bottom face and a side wall and housing the slurry, characterized in that the slurry is extracted from an open end of a slurry extraction tube provided at the side wall of the agitation vessel. More preferably, a normal line direction of a surface of the open end is in a direction of an angle with respect to a downstream direction of a flow of the slurry caused by agitation of 0° or more and less than 90°.

6 Claims, 3 Drawing Sheets

(a)

(b)

(a)

(b)

(a)

(b)

METHOD FOR EXTRACTING SLURRY

TECHNICAL FIELD

The present invention relates to an extracting method capable of extracting slurry stably for a prolonged period of time from an agitation vessel housing the slurry.

BACKGROUND ART

Slurry is handled in various scenes in chemical industries. Some problems occur on handling slurry due to solid contained in slurry. One of the problems is that it is necessary that slurry is flowed consistently for preventing solid contained in the slurry from being sedimented in a vessel. Accordingly, slurry is generally housed in an agitation vessel having an agitator.

In the case where crystals are formed and/or grown in slurry, however, i.e., a liquid phase constituting the slurry has dissolving power to crystals in the slurry, such a phenomenon frequently occurs that crystals are accumulated on the wall of the agitation vessel and the agitation blade. This is because not only crystals in the slurry are sedimented, but also crystals newly deposited from the liquid phase are bound with the crystals thus sedimented and then agglomerated to form large-sized solid matters.

The accumulated matters may be released from the wall of the vessel due to impact or the like and may be mixed into the slurry. The released accumulated matters are generally not broken into the size of the crystals in the slurry, and are often present therein as an agglomerate having been released as it is or a pulverized matter thereof.

Extraction of slurry is generally carried out through an extraction tube provided at a bottom of the vessel for preventing dead space from occurring. The open end of the extraction tube is generally at the same position as the bottom of the vessel. The agglomerate or pulverized matter thereof may flow into the extraction tube to cause flowage failure or to cause complete obstruction. Various kinds of agitation devices have been proposed, but it is technically difficult to obtain a completely mixed state of slurry by agitation. In particular, such a phenomenon cannot be avoided that solid contained in the slurry is locally sedimented, and the solid may flow into the extraction tube to cause flowage failure or obstruction of the extraction tube. The flow rate is quickly increased at the part where the slurry enters the extraction tube from the vessel. Accordingly, a solid matter having a large weight remains at the extraction part where the change in flow rate becomes maximum, whereby the solid matter may form a bridge at the inlet of the extraction tube to cause flowage failure or obstruction of the extraction tube.

For example, in a process of producing terephthalic acid through hydrolysis of dimethyl terephthalate in an agitation vessel, the most part of terephthalic acid produced is suspended as crystals in an aqueous solution since the solubility of terephthalic acid in the aqueous solution is relatively small under the reaction condition. A part of the crystals is accumulated on the wall of the reaction vessel or an agitator to form a stiff solid matter. When the solid matter is released due to impact or the like and mixed into the slurry, the solid matter may flow into the extraction tube at the bottom of the vessel to fail to send the slurry due to obstruction of the extraction tube.

In a process of continuously sending slurry from an agitation vessel to another agitation vessel under a lower pressure through a decompression valve, the obstruction is liable to occur since the decompression valve has a part having a narrower flow path than the tube.

In order to solve the problem, Patent Document 1 proposes such a measure that an open end of an extraction tube, which is provided at a bottom of a vessel, is provided to protrude from the bottom by 50 mm or more. However, such an agitator is also proposed that cannot have an open end protruding from the bottom by 50 mm or more, depending on the configuration of the agitator, and the application range thereof is limited.

(Patent Document 1) JP-A-8-141386

DISCLOSURE OF THE INVENTION (Problems to be solved by the Invention)

The invention has been made in view of the aforementioned related art, and an object thereof is to provide such a method for extracting slurry that is not inhibited in extraction of slurry by a released and accumulated matter or a solid matter sedimented and accumulated at the bottom of the vessel.

(Means for Solving the Problems)

As a result of earnest investigations made by the inventors for solving the problems, it has been found that extraction of slurry can be carried out without inhibition due to a sedimented and accumulated solid matter by using an apparatus having a particular constitution, and thus the invention has been completed.

According to the investigation by the inventors, the invention relates to "a method for extracting slurry by extracting slurry from an agitation vessel having a bottom face and a side wall and housing the slurry, characterized in that the slurry is extracted from an open end of a slurry extraction tube provided at the side wall of the agitation vessel", whereby the slurry extraction tube can be prevented from suffering from obstruction to attain the object.

In a preferred embodiment, the open end of the slurry extraction tube protrudes from the side wall of the agitation vessel in a direction toward an interior of the agitation vessel. In this embodiment, a released matter and a sedimented solid content can be prevented from flowing into the slurry extraction tube, and thus extraction of slurry can be prevented from being inhibited.

It is preferred that the slurry flows in the agitation vessel, and the slurry extraction tube is provided to protrude from the side wall of the agitation vessel in a direction toward an interior of the agitation vessel, with a normal line direction of a surface of the open end of the slurry extraction tube being in a direction of an angle with respect to a downstream direction of a flow of the slurry of 0° or more and less than 90°, preferably from 0° to 60°, and more preferably 0° or more and less than 30°. In this embodiment, an eddy current is formed in the vicinity of the open end surface in the downstream side, and formation of a solid bridge at the slurry extraction tube can be prevented by the agitation effect of the eddy current.

ADVANTAGES OF THE INVENTION

According to the method for extracting slurry of the invention, the slurry extraction tube is provided at the side wall of the agitation vessel, so as to prevent inhibition in extraction of slurry due to obstruction of the slurry extraction tube with a released agglomerate of crystals accumulated on the wall of the agitation vessel or the agitation blade and accumulation of a solid matter on the slurry extraction tube.

The open end of the slurry extraction tube protrudes from the side wall of the agitation vessel in a direction toward the interior of the agitation vessel, or furthermore the normal line direction of the open end surface is in a direction of an angle with respect to the downstream direction of a flow of the slurry of 0° or more and less than 90°, whereby an eddy current is formed in the downstream side of the protruding part of the slurry extraction tube, and thus formation of a solid bridge at the slurry extraction tube can be prevented from occurring by the agitation effect of the eddy current.

BEST MODE FOR CARRYING OUT THE INVENTION

Figure 1:
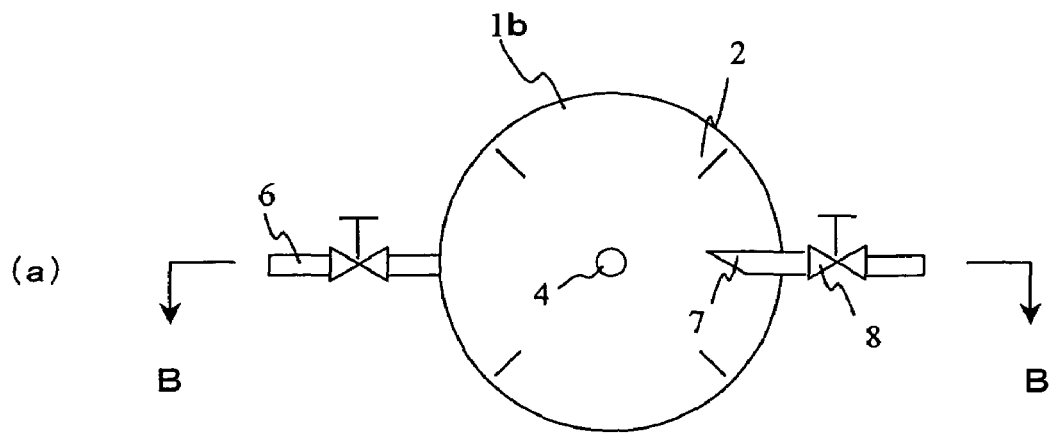
FIG. 1 is a schematic illustration showing an example of an agitation vessel used upon practicing the method for extracting slurry according to the invention.
Figure 1:
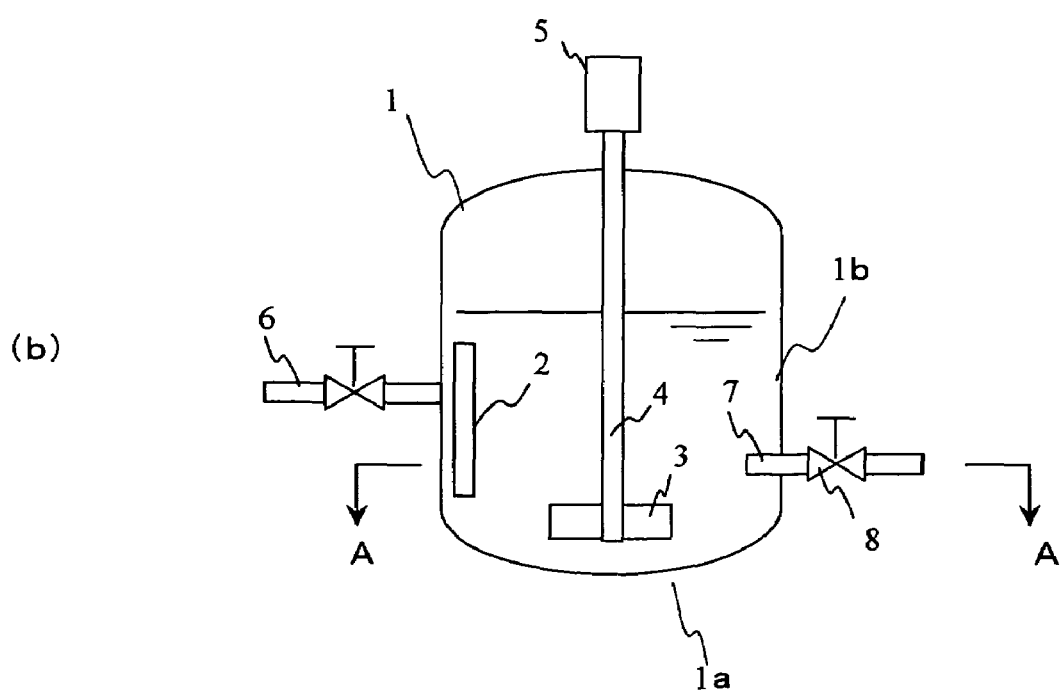

Embodiments of the invention will be described below with reference to the drawings. FIG. 1 shows an example of an agitation vessel in an embodiment of the invention. Fig. (a) is a horizontal cross sectional view on line A-A in Fig. (b), and Fig. (b) is a vertical cross sectional view on line B-B in Fig. (a). FIG. 1 shows that an agitation vessel 1 is formed in a vertical cylindrical shape, and the agitation vessel has a bottom face 1a and a side wall 1b. The agitation vessel further has a baffle 2 in the vertical direction along the inner wall of the side wall 1b. An agitation blade 3 is provided in the vertical direction at the center of the agitation vessel 1. A rotation axis 4 of the agitation blade extends upward through an upper wall of the agitation vessel 1 and is driven by a driving unit 5.

A raw material introduction path 6 is connected to an intermediate part of the agitation vessel 1. A slurry extraction tube 7 is provided at the side wall 1b of the agitation vessel 1, preferably in such a state that the slurry extraction tube 7 protrudes from the side wall 1b of the agitation vessel in a direction toward the interior of the agitation vessel. The slurry is extracted through a decompression valve 8 depending on necessity.

The method of the invention is preferably applied to slurry containing terephthalic acid and a liquid. Preferred examples of the liquid include water and a glycol compound, such as ethylene glycol, propylene glycol, tetramethylene glycol and diethylene glycol, and water is most suitable since it is inexpensive and is easy to handle.

An example will be described, in which slurry of terephthalic acid is produced by hydrolyzing dimethyl terephthalate by using the aforementioned apparatus. Dimethyl terephthalate and water are introduced into an agitation vessel (which is used as a hydrolysis reaction vessel) 1 through a raw material introducing path 6. Hydrolysis reaction is then carried out under stirring by rotating an agitation blade 3 with a driving unit 5. At this time, the system may be heated depending on necessity. Dimethyl terephthalate is hydrolyzed through hydrolysis reaction to form terephthalic acid, which is deposited as crystals in the agitation vessel. Accordingly, slurry containing terephthalic acid and water is formed in the agitation vessel. The slurry is extracted through a slurry extraction tube 7 and sent to a subsequent hydrolysis reactor or a tank.

Figure 2:
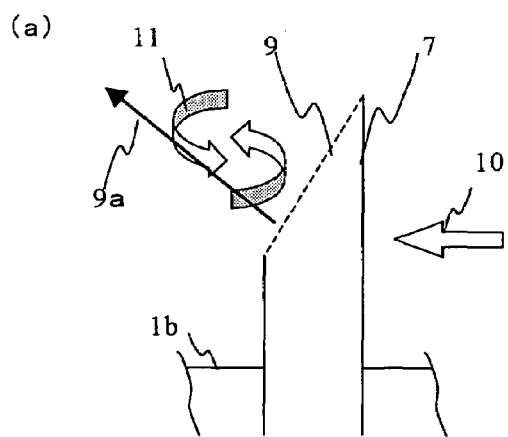
FIGS. 2 to 9 are schematic illustrations showing specific shapes of an open end of a slurry extraction tube.
Figure 2:
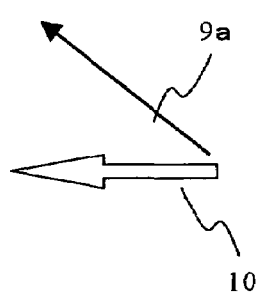

The reaction liquid, i.e., the slurry containing the crystals, is circulated along the inner wall of the reaction vessel through agitation with the agitator. FIG. 2 is an enlarged view of a tip end part of the slurry extraction tube 7 shown in FIG. 1(a). As shown in FIG. 2(a), the slurry extraction tube 7 is made protrude inward from the side wall 1b of the agitation vessel, and a normal line direction 9a of an open end surface 9 is disposed to provide an angle with respect to the downstream direction 10 of the flow of the slurry caused by agitation of 0° or more and less than 90°, preferably from 0° to 60°, and more preferably 0° or more and less than 30° (see FIG. 2(b)). According to the constitution, an eddy current 11 is formed in the vicinity of the open end surface of the slurry extraction tube to obtain a sufficient agitation effect of the slurry. Accordingly, the formation of a bridge of crystal solid in the vicinity of the open end surface of the slurry extraction tube is suppressed.

As shown in FIG. 3(a), on the other hand, in the case where the normal line direction 9a of the open end surface 9 of the slurry extraction tube 7 is disposed to provide an angle with respect to the downstream direction 10 of the flow of the slurry or 90° or more (see FIG. 3(b)), an eddy current 11 formed in the downstream side of the slurry extraction tube is formed on the backside of the open end surface to fail to obtain the agitation effect of the slurry.

Figure 3:
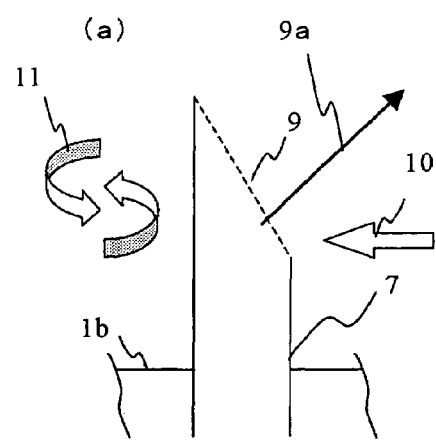
Figure 3:
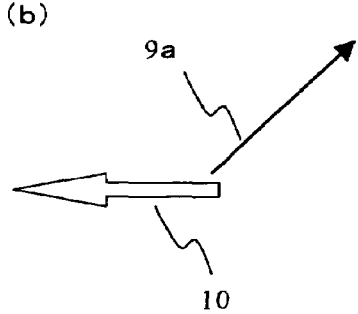
Figure 4:
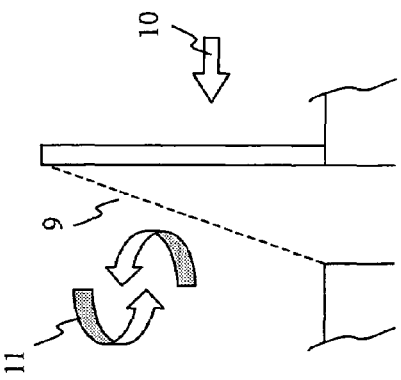
Figure 5:
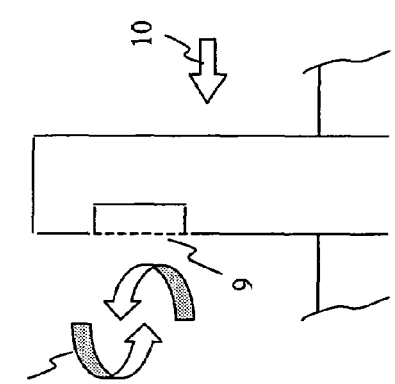
Figure 6:
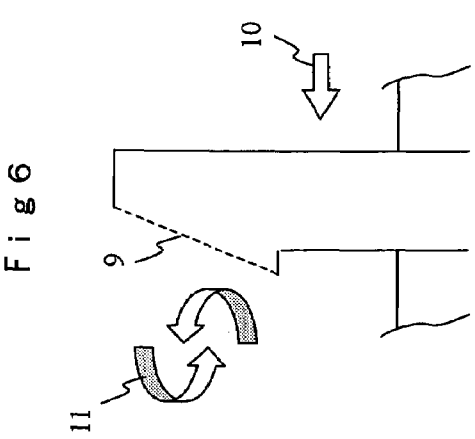
Figure 7:
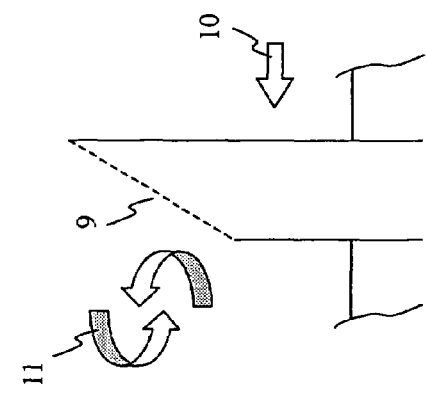
Figure 8:
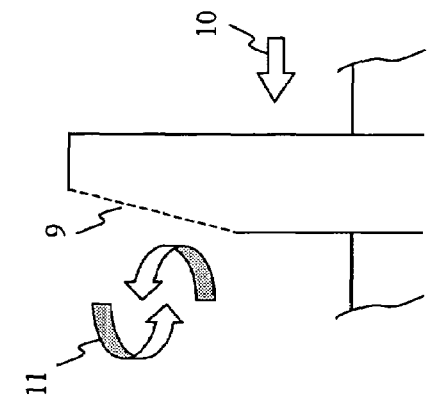
Figure 9:
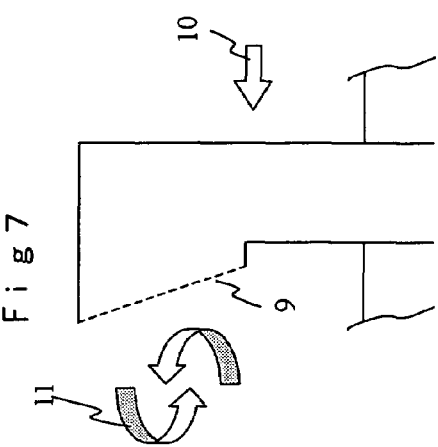

The flow of the slurry is not limited to a flow caused only for agitation and may be a flow of the slurry caused upon introducing into the agitation vessel. While FIGS. 2 and 3 show the cases where the angle of the normal line direction of the open end surface with respect to the downstream direction of the flow of the slurry is clockwise, it is not limited to clockwise but may be counterclockwise (see FIG. 7).

FIGS. 4 to 9 are embodiment illustrations of preferred shapes of the protruding part of the slurry extraction tube according to the invention.

It is preferred in the method of the invention that the slurry is extracted from an agitation vessel to another agitation vessel under a lower pressure through a decompression valve. The extraction rate of the slurry can be increased by utilizing a difference in pressure between the agitation vessel, from which the slurry is extracted, and the agitation vessel, to which the slurry is extracted. Specifically, the pressures of the two agitation vessels are preferably set to provide a difference in pressure of 0.1 MPa or more, and more preferably 0.5 MPa or more. The decompression valve is not particularly limited, and an ordinary decompression valve may be used.

It is also preferred in the method of the invention that the slurry is extracted by aspirating with a pump. It is a preferred embodiment since the extraction rate of the slurry can be increased. The pump is not particularly limited, and an ordinary pump for transmitting a liquid may be used.

EXAMPLES

The invention will be described more specifically with reference to examples, but the invention is not construed as being limited thereto.

Example 1

In an equipment for producing terephthalic acid through hydrolysis reaction of dimethyl terephthalate, the hydrolysis reaction was carried out with a four-step continuous vessel reactor having plural agitation vessels each having the agitator shown in FIG. 1. Slurry having a temperature of about 250° C., a pressure of 4 MPa and a slurry concentration of about 50% by weight in the first step reaction vessel was continuously transmitted through a decompression valve to the second step reaction vessel having been maintained at a temperature of about 235° C. and a pressure of 3 MPa. Subsequently, the terephthalic acid slurry in the second step reaction vessel was aspirated with a pump and continuously transmitted to the third step reaction vessel having been maintained at a temperature of about 235° C. and a pressure of 3 MPa. Subsequently, the terephthalic acid slurry in the third step reaction vessel was continuously transmitted through a decompression valve to the fourth step reaction vessel having been maintained at a temperature of about 220° C. and a pressure of 2.2 MPa. Subsequently, the terephthalic acid slurry in the fourth step reaction vessel was continuously transmitted through a decompression valve to a slurry storage tank having been maintained at a temperature of about 100° C. and the atmospheric pressure.

At this time, the slurry extraction tubes in the respective reaction vessels were disposed at such a position that is at the side wall of the agitation vessel and is always lower than the liquid surface of the slurry, in the reaction vessel. Simultaneously, the slurry extraction tubes were disposed to provide an angle of the normal line direction of the open end surface of the slurry extraction tube with respect to the downstream direction of the flow of the slurry, caused by agitation of 30°. Upon transmitting the terephthalic acid slurry by using the reaction vessels, the operation could be stably carried out for four months without obstruction.

Example 2

The continuous vessel reactor as in Example 1 was prepared except that the slurry extraction tubes were disposed to provide an angle of the normal line direction of the open end surface of the slurry extraction tube with respect to the downstream direction of the flow of the slurry caused by agitation of 0°. In other words, a slurry extraction tube having the shape of the open end surface shown in FIG. 8 was used. Upon transmitting the slurry by using the apparatus, the operation could be stably carried out for four months without obstruction.

Example 3

The continuous vessel reactor as in Example 1 was prepared except that the slurry extraction tubes were disposed to provide an angle of the normal line direction of the open end surface of the slurry extraction tube with respect to the downstream direction of the flow of the slurry caused by agitation of 60°. Upon transmitting the slurry by using the apparatus, the operation could be stably carried out for four months without obstruction while the extraction amount of the slurry was lowered to an amount of 85% based on that at the time of initiating the transmission.

Comparative Example 1

The slurry was transmitted by using the apparatus of Example 1 except that the position of extracting the slurry from the preceding agitation vessel was disposed at the center of the bottom face of the reactor, and as a result, extraction of the slurry became impossible after 5 hours to fail to continue the operation.

INDUSTRIAL APPLICABILITY

The method for extracting slurry of the invention can suppress inhibition of extraction of slurry due to a released accumulated matter and a sedimented and accumulated solid matter, and thus extraction can be carried out extremely stably, whereby it is applicable to various fields where slurry is handled.

The invention claimed is:

1. A method for extracting slurry by extracting slurry from an agitation vessel having a bottom face and a side wall and housing the slurry, characterized in that the slurry is extracted from an open end of a slurry extraction tube provided at the side wall of the agitation vessel;
   wherein the open end of the slurry extraction tube protrudes from the side wall of the agitation vessel in a direction toward an interior of the agitation vessel;
   wherein the slurry flows in the agitation vessel, and a normal line direction of a surface of the open end of the slurry extraction tube is in a direction of an angle with respect to a downstream direction of a flow of the slurry of 0° or more and less than 90°;
   wherein the slurry comprises terephthalic acid and water, ethylene glycol, propylene glycol, tetramethylene glycol or diethylene glycol; and
   wherein the slurry is extracted from the agitation vessel to another agitation vessel under a lower pressure through a difference in pressure of 0.1 MPa or more.

2. The method for extracting slurry as claimed in claim 1, wherein the slurry flows in the agitation vessel, and a normal line direction of a surface of the open end of the slurry extraction tube is in a direction of an angle with respect to a downstream direction of a flow of the slurry of from 0° to 60°.

3. The method for extracting slurry as claimed in claim 1, wherein the slurry flows in the agitation vessel, and a normal line direction of a surface of the open end of the slurry extraction tube is in a direction of an angle with respect to a downstream direction of a flow of the slurry of 0° or more and less than 30°.

4. The method for extracting slurry as claimed in claim 1, wherein the slurry is extracted through a decompression valve to a vessel under a pressure lower than the agitation vessel.

5. The method for extracting slurry as claimed in claim 1, wherein the slurry is extracted by aspirating with a pump.

6. The method for extracting slurry as claimed in claim 1, wherein the terephthalic acid is obtained through hydrolysis of dimethyl terephthalate.

* * * * *